United States Patent [19]

Peacock

[11] Patent Number: 4,720,097
[45] Date of Patent: Jan. 19, 1988

[54] SIMULATED WORK ENVIRONMENT ABILITY TESTER

[76] Inventor: Claude F. Peacock, 2433 Dalton Dr., Pelham, Ala. 35124

[21] Appl. No.: 902,795

[22] Filed: Sep. 2, 1986

[51] Int. Cl.$^4$ ............................................. A63B 21/06
[52] U.S. Cl. .................................... 272/118; 272/134
[58] Field of Search ................... 272/134, 130, 62, 118

[56] References Cited

U.S. PATENT DOCUMENTS 3,746,338  7/1973  Proctor .............................. 272/62 X
3,752,473  8/1973  Lalanne ................................. 272/62
4,540,171  9/1985  Clark .................................... 272/118

FOREIGN PATENT DOCUMENTS 2561528  9/1985  France ................................ 272/134

Primary Examiner—Dave W. Arola
Attorney, Agent, or Firm—Jennings, Carter, Thompson & Veal

[57] ABSTRACT

A simulated work environment ability tester utilizes an upright frame on which a plurality of projections are spaced as scale to determine a worker's range of motion. The projections cooperate with a resistively biased bar to allow evaluation of the strength and endurance of a worker to determine his suitability to perform specified tasks. A movable platform supported on the frame allows evaluation of the worker's aptitudinal skills in a simulated work station. Each member of the apparatus may be made of lightweight material and adapted for easy assembly, thereby making the device amenable to use in a variety of locations.

12 Claims, 1 Drawing Figure

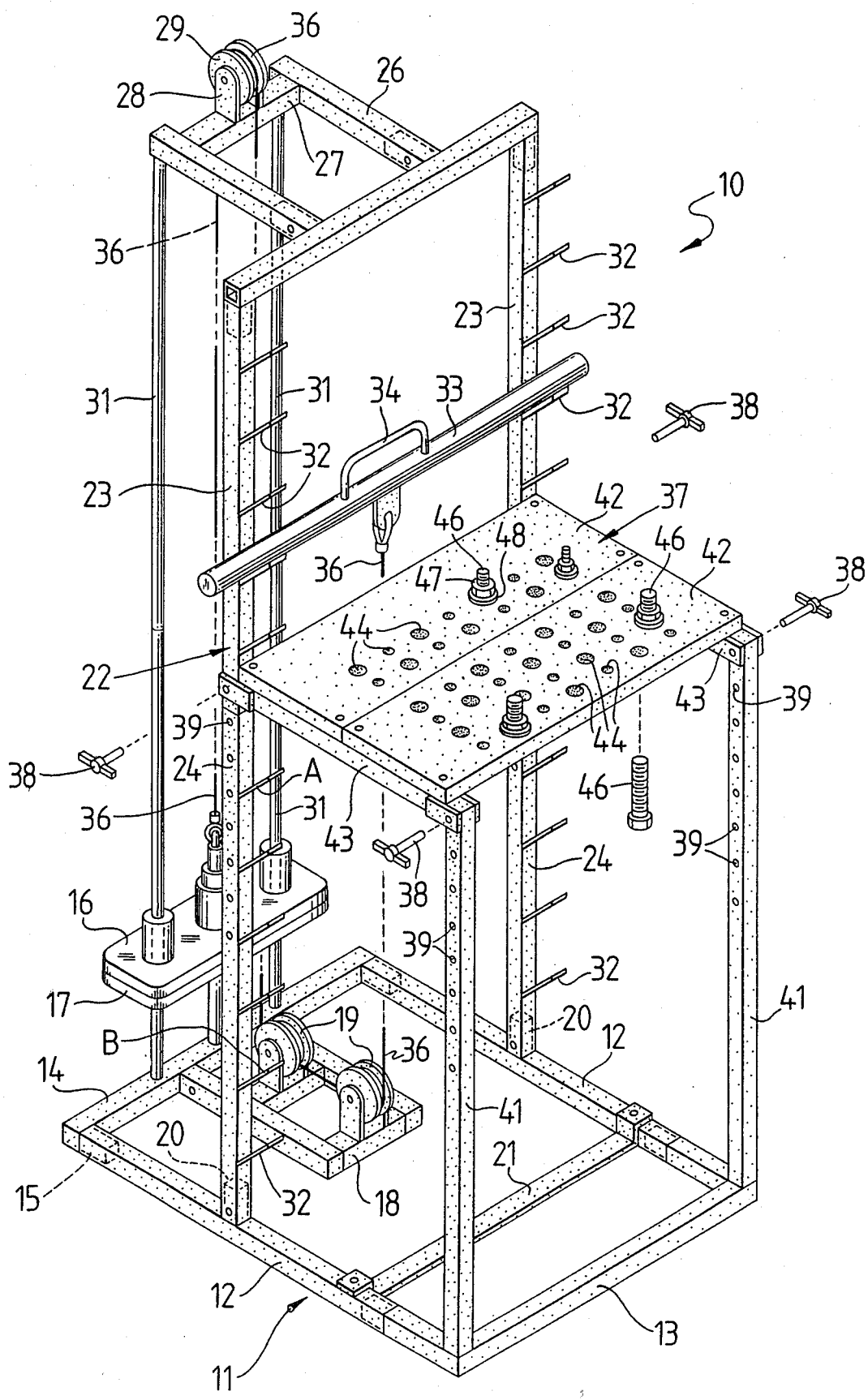

SIMULATED WORK ENVIRONMENT ABILITY TESTER

FIELD OF THE INVENTION

The present invention relates to the field of vocational rehabilitation and assessment. More particularly the present invention relates to the testing of individuals to determine the parameters of vocational disability by means of an objective and quantitative measure. In even greater particularity, the present invention relates to apparatus used to simulate a work environment to provide a repeatable test bed for vocational capability testing.

BACKGROUND OF THE INVENTION

Vocational rehabilitation specialists are oftentimes required to evaluate the vocational capabilities or disabilities of an individual subsequent to the individual being injured or having suffered certain health problems. At other times, such evaluations may occur as an ongoing effort to increase productivity by matching a worker's physical capabilities with a particular job requirement. In many instances such evaluations are hampered by a lack of objective criteria upon which the specialist can appraise the worker's vocational capabilities. To meet this need, certain test devices have been offered for use by the specialist. The known devices are exceedingly complex and prohibitively expensive for the average practitioner.

Furthermore, the known devices are not readily transported. Therefore, a need exists for a low cost portable device which can serve as an objective test bed upon which a worker's capabilities can be accurately evaluated.

SUMMARY OF THE INVENTION

It is the object of the present invention to provide a simulated work station wherein the capabilities of a worker to perform routine tasks associated with his job requirements can be objectively evaluated.

Another object of the present invention is to provide a simulated work station which can replicate the work requirements of a number of actual work stations.

Yet another object of the present invention is to provide a simulated work station with the above characteristics, which is portable and inexpensive.

My invention advantageously meets these objects and others through the use of a lightweight construction and a generic design philosophy. The primary aspects of vocational evaluation which my apparatus is designed to assist with are generally defined as the isotonic lifting assessment and the aptitudinal screening assessment. The isotonic lifting assessment includes evaluation of the worker's range of motion in the lifting profile from floor level to overhead, a strength assessment through intervals of the range of motion, and an endurance assessment based on repetitive lifting of a predetermined weight through a predetermined range.

The aptitudinal screening assessment includes simple manual dexterity assessment, fine dexterity assessment, motor coordination and speed, eye-hand coordination, and tool usage ability.

My apparatus simulates the work station range of motion requirement with a vertical frame on which a plurality of spaced apart projections form a scale extending from floor level to overhead. An indicator bar is provided which may be supported on said projections at any height on the frame. To test the strength of the worker, the indicator bar is attached to a means for biasing the bar to resist vertical movement, such as a weight and pulley system. Also supported on the frame is a work platform on which a plurality of work pieces are disposed. The platform is adjustably supported on the frame such that it may be positioned to simulate a work surface at any desired level. The simulated work pieces are preferably a plurality of common fasteners which can be used to assess motor skills, dexterity and hand-eye coordination at various levels.

The frame is made of tubular metal components to provide high strength and light weight and may be completely dismantled for storage or transport.

BRIEF DESCRIPTION OF THE DRAWINGS

The FIGURE is a perspective view of an apparatus embodying features of my invention.

DESCRIPTION OF A PREFERRED EMBODIMENT

The simulated work environment ability tester 10 shown in the FIGURE utilizes square metal tubing as the major structural components. It is to be understood that the choice of material for the component structure is limited only by consideration of weight and strength insofar as my apparatus is intended to be portable, and thus must be easily assembled or disassembled.

The tester 10 includes a base 11 defined by a pair of side members 12, a front member 13, and a rear assembly 14. The rear assembly 14 includes a weight stack 16 resting on a cross member 17 and a lower pulley bracket 18 carrying a pair of pulleys 19. A foot rest 21 extends between the side members 12. The front member 13 and rear assembly 14 are cooperatively shaped to connect to the side members 12 by telescopically sliding within the respective ends of the side members 12, as shown at 15.

The side members 12 support an upright frame 22 which includes upper and lower side members 23 and 24 and an upper rear assembly 26. Upper rear assembly 26 includes a cross member 27 and an upper pulley bracket 28 which carries a pulley 29. A set of guide rods 31 extend from the lower pulley bracket 18 to upper pulley bracket 28 and are slidingly engaged by the weight stack 16. Each member of the frame 22 is formed as indicated at 20, to cooperatively telescopically interfit in the same manner as the base 11. The upper and lower side members 23 and 24 carry a plurality of upwardly projecting hanger elements 32 which are spaced from the base 11 to the cross member 27. The hanger elements 32 are spaced such that multiples of the intervals therebetween provide common ranges through which a worker must lift an object. For example, with a six inch spacing, a worker's normal lifting range of 36 inches from the floor for his particular job would be simulated by a lifting motion between the floor and the hanger element labeled "A" in the FIGURE. A bar 33 serves as an indicator and is movable from one set of hanger elements to another to determine the range of motion as will be described hereafter. The bar 33 may be provided with a handle 34 to facilitate testing of one arm at a time. To assess strength and/or endurance, the bar 33 is connected to the weight stack 16 by a cable 36 which runs over pulleys 19 and 29. Of course, the weight stack 16 is variable in the amount of weight to be lifted. Also, although a weight stack is depicted, it should be understood that any means for biasing the bar 33 to resist upward movement may be used. For example, the bar 33 may be so biased using hydraulic cylinders, spring cylinders, elastic bands, or electromagnetic means as are well known.

A platform 37 is provided to simulate a countertop, table top, or overhead partition. The platform 37 is supported by pins 38 inserted in cooperative apertures 39 formed in the upright members 23 and 24 and a pair of legs 41 connected to the platform 37 distal the frame 22. The platform 37 preferentially has two or more panels 42 supported on runners 43 connected between the frame 22 and the legs 41. The panels 42 have a plurality of apertures 44 therein through which cooperatively sized bolts 46 are inserted. Each bolt 46 is engaged by a nut 47 and is provided with a washer 48. The bolt, nut, and washer combination simulates a work piece and is used to test dexterity, motor skills, and coordination.

It is to be understood that my apparatus is passive, requiring no external power, and dependent solely on the capabilities of the person being tested. Thus each individual tested is tested with exactly the same work environment and condition. The practitioner will see that the apparatus is suited for testing numerous aspects of the individual's vocational capabilities for comparison with established norms for a particular job or function. The following examples are not intended as a comprehensive listing of the evaluation procedures in which my invention may be employed.

Range of Motion Testing

Range of motion testing is a basic test which is easily performed with my invention. The bar 33 is disconnected from the cable 36 and placed on one of the sets of the hanger elements 32. The individual to be tested is then required to iteratively move the bar 33 to an adjacent set of hanger elements until the bar 33 has been moved to each set of hanger elements 33. The sequence may be performed with one or both hands and the platform 37 may be interposed between the individual and the frame at a selected height or may be removed as desired.

Strength and Endurance Testing

Strength and endurance testing is performed with the cable 36 attached to the bar 33 and the weight stack 16 set to simulate the weight to be lifted at a particular work station. Strength is tested by requiring the individual to move the bar 33 from one set of selected hanger elements 32 to another selected set of hanger elements 32, with the space between the elements 32 corresponding to the distance an object must be moved at a work station. For example, the distance between the element labeled "B" and the element labeled "A" is twenty-four inches and corresponds to lifting an object resting one foot off the ground to a height of three feet.

Endurance testing may be nothing more than iterative strength testing in which the bar 33 is repetitively moved between the selected hanger elements 32 until fatigue or pain limitations are observable. In either strength or endurance testing, the platform may be positioned in accordance with the particular norms of the job as an obstacle or reference plane or may be removed as desired.

Aptitudinal Screening

A variety of aptitudinal skills may be evaluated using the platform 37 and the simulated work pieces. In each instance, the platform 37 is positioned at a height corresponding to a work surface such as a table, curb, or counter top. The individual may be seated or standing as required by the particular job and is asked to manipulate the work pieces in a prescribed manner, such as inserting the bolts 46 through the apertures 44 and securing them with nuts 47 in a particular pattern or in a particular direction or with the dominant hand performing a particular function. The size of the work pieces used assists the evaluator in determining both simple manual dexterity and fine dexterity. The individual may also be required to manipulate the work pieces with a tool such as a wrench or nut driver.

Each of these tests could be performed independently by other means, however, the use of my invention permits the exact duplication of each test in a work station which remains identical from one test subject to another, thereby assuring an objective evaluation of each subject's skills, capabilities, and disabilities. Furthermore, my invention may simulate any of a number of work environments by varying the range of motion requirements, strength requirements, and platform location. Therefore, numerous workers having different jobs may be evaluated using the same apparatus or a single worker can be evaluated in a controlled environment simulating his particular job. Since the invention is lightweight and easily assembled, it may be easily transported for use in the evaluator's office, in a manufacturing or warehouse facility, in a hospital, or in a courtroom. Thus the invention provides a unique and inexpensive tool to be used for the practitioner.

While I have shown my invention in one form, it will be obvious to those skilled in the art that it is not so limited but is susceptible of various changes and modifications without departing from the spirit thereof.

What I claim is:

1. Apparatus for measuring the vocational capabilities of a person comprising in combination:
    (a) graduated means for indicating the isotonic lifting capabilities of said person throughout a normal range of motion; and
    (b) skill means for indicating the aptitudinal abilities of said person in terms of manual dexterity including a platform detachably affixed to said graduated means at any one of a plurality of predetermined heights to simulate a work station and a plurality of work simulation pieces detachably affixed to said platform.

2. Apparatus as defined in claim 1 wherein said platform includes a plurality of apertures for receiving said work pieces and said work pieces comprise fasteners of predetermined size for insertion into said apertures.

3. Apparatus as defined in claim 2 wherein said apertures are arranged in a predetermined pattern.

4. Apparatus as defined in claim 1 wherein said graduated means comprises:
    (a) at least one vertical member;
    (b) a plurality of evenly spaced hangers on said vertical member defining graduation in a vertical range of motion extending from floor level upwards;
    (c) an indicator, manually movable into engagement with a selected hanger; and
    (d) means for biasing said indicator to resist movement vertically.

5. Apparatus as defined in claim 4 wherein said means for biasing is variable such that different amounts of force may be required to move said indicator.

6. Apparatus for measuring vocational capabilities of a person comprising:
 (a) an upright frame having a plurality of vertically spaced hangers thereon;
 (b) a movable indicator engageble, by manual force, with said hangers;
 (c) means for biasing said indicator to resist vertical movement;
 (d) a platform detachably affixed to said upright frame at any one of a plurality of predetermined heights to simulate a work station; and
 (e) a plurality of work simulation pieces detachably affixed to said platform.

7. Apparatus as defined in claim 6 wherein said means for biasing is adjustable within a predetermined range of resistive forces.

8. Apparatus as defined in claim 6 wherein said movable indicator is a bar adapted for engagement with said hangers.

9. Apparatus as defined in claim 6 wherein said hangers are spaced at known intervals such that movement of said indicator between selected hangers defines a selected range of motion.

10. Apparatus as defined in claim 6 wherein said frame comprises:
 (a) a detachable base portion;
 (b) detachable upright members supported on said base portion and supporting said hangers; and
 (c) a detachable upper portion connecting said upright members at the tops thereof.

11. Apparatus as defined in claim 10 wherein said platform is supported by said upright members.

12. Apparatus as defined in claim 6 wherein said plurality of simulated work pieces comprise a plurality of bolts and washers cooperatively sized in various sizes to be inserted through and secured to said platform in a predetermined pattern of apertures.

* * * * *